United States Patent [19]

Hardt

[11] 4,196,287

[45] Apr. 1, 1980

[54] PROCESS FOR THE CATALYTIC PRODUCTION OF 2-SUBSTITUTED PYRIDINES

[75] Inventor: Peter Hardt, Visp, Switzerland

[73] Assignee: Lonza Ltd., Gampel, Switzerland

[21] Appl. No.: 843,033

[22] Filed: Oct. 17, 1977

Related U.S. Application Data

[63] Continuation-in-part of Ser. No. 724,939, Sep. 20, 1976, abandoned.

[30] Foreign Application Priority Data

Sep. 18, 1975 [CH]  Switzerland ..................... 12139/75
Oct. 15, 1976 [CH]  Switzerland ..................... 013079/76
Aug. 2, 1977 [CH]  Switzerland ..................... 009471/77

[51] Int. Cl.² .................. C07D 213/08; C07D 213/74
[52] U.S. Cl. ..................................... 544/124; 546/253; 546/252; 546/193; 546/281; 546/304; 544/124; 544/331; 546/250

[58] Field of Search ............ 260/290 P, 294.9, 296 D, 260/256.4 R, 293.69; 544/124; 546/193, 252, 253, 281, 304, 250

[56] References Cited

U.S. PATENT DOCUMENTS

| 3,829,429 | 8/1974 | Clement ........................... 260/290 P |
| 4,006,149 | 2/1977 | Bonnemann et al. ............ 260/290 P |

OTHER PUBLICATIONS

Wakatsuki et al., "Synthesis", 1976 (Jan.), No. 1, pp. 26–28.

*Primary Examiner*—Alan L. Rotman
*Assistant Examiner*—Robert T. Bond
*Attorney, Agent, or Firm*—Fisher, Christen & Sabol

[57] ABSTRACT

A process for the catalytic production of a 2-substituted pyridine which comprises reacting a corresponding cyano compound and acetylene in the presence of cobaltocene. Favorable conversion speed, conversion of at least 90 percent, good yield and high selectivity are obtained.

21 Claims, No Drawings

PROCESS FOR THE CATALYTIC PRODUCTION OF 2-SUBSTITUTED PYRIDINES

This application is a continuation-in-part of application Ser. No. 724,939, filed on Sept. 20, 1976, now abandoned.

BACKGROUND OF THIS INVENTION

1. Field of This Invention

This invention relates to a process for the catalytic production of 2-substituted pyridines from the correspondingly substituted cyano compounds and acetylene using a cobalt catalyst.

2. Prior Art

It is known to produce 2-substituted pyridines from the corresponding carboxylic acid nitriles and acetylene in the presence of the catalyst cyclopentadienyl-(triphenylphosphine)-cobaltatetraphenylcyclopentadiene or cyclopentadienyl-(cobalt-triphenylphosphine)cobalt diphenyl acetylene at yields of about 23 or 16 percent, respectively [Tetrahedron Letters No. 36, (1973), pp. 3383 and 3384].

Furthermore, methyl heptadienyl-cobalt(I)-butadiene [Synthesis, (1974), p. 575] and a number of other cobalt compounds (U.S. Pat. No. 3,829,429) have been proposed as catalysts for these systems. See also U.S. Pat. No. 4,006,149.

The previously proposed or used catalysts, however, provide uneconomical processes because of insufficient conversions and yields, as well as because of complicated multi-step production methods or insufficient thermal stability of the catalysts.

BROAD DESCRIPTION OF THIS INVENTION

An object of this invention is to provide a process for the catalytic production of 2-substituted pyridines from the correspondingly substituted cyano compounds and acetylene which has very high conversions, high selectivity, good conversion speeds and high yields. Other objects and advantages of this invention are set out herein or are obvious herefrom to one ordinarily skilled in the art.

The objects and advantages of this invention are achieved by the process of this invention.

This invention is based in part on the discovery that bis-cyclopentadienyl-cobalt (i.e., cobaltocene) is eminently suitable for use as a catalyst for the production of 2-picoline and 2-substituted pyridines. This catalyst is easy to handle and, as is well known, can be produced easily from simple educts. A particular advantage in the use of cobaltocene as a catalyst consists in the fact that this catalyst can be used at high temperatures (above 80° C.). With such advantage quicker and more complete conversions of the cyano compounds are achieved, without promoting the known side reactions of the acetylene with itself to benzene and polymers.

This invention relates to a process for the production of 2-substituted pyridines from the corresponding cyano compounds and acetylene at conversions of at least 90 percent, good yields and high selectivity, characterized in that the reaction is carried out at a temperature above 80° C. in the presence of cobaltocene.

Cyano compounds which can be used as starting materials in the process of this invention are those which have the formula:

wherein A is alkyl having 1 to 8 carbon atoms, preferably 1 to 4 carbon atoms, cycloalkyl having 3 to 9 carbon atoms, alkenyl having 2 to 8 carbon atoms, aryl having 6 to 10 carbon atoms, cyanoaryl wherein the aryl moiety has 6 to 10 carbon atoms, pyridyl, pyrimidyl or

wherein $R_1$ is hydrogen or alkyl having 1 to 6 carbon atoms, preferably 1 to 4 carbon atoms, $R_2$ is hydrogen or alkyl having 1 to 6 carbon atoms, preferably 1 to 4 carbon atoms, and $R_3$ is cyanoalkyl wherein the alkyl moiety has 1 to 6 carbon atoms, preferably 1 to 4 carbon atoms, carbalkoxy alkyl wherein the alkyl moiety has 1 to 6 carbon atoms, preferably 1 to 4 carbon atoms, or aralkyl wherein the alkyl moiety preferably has 1 to 6 carbon atoms, and the aryl moiety has 6 to 10 carbon atoms, or wherein $R_1$ is hydrogen or alkyl having 1 to 6 carbon atoms, preferably 1 to 4 carbon atoms, $R_2$ is cyanoalkyl wherein the alkyl moiety has 1 to 6 carbon atoms, preferably 1 to 4 carbon atoms, carbalkoxyalkyl wherein the alkyl moiety has 1 to 6 carbon atoms, preferably 1 to 4 carbon atoms, or aralkyl wherein the alkyl moiety has 1 to 6 carbon atoms, preferably 1 to 4 carbon atoms, and the aryl moiety has 6 to 10 carbon atoms, and $R_3$ is cyanoalkyl wherein the alkyl moiety has 1 to 6 carbon atoms, preferably 1 to 4 carbon atoms, carbalkoxyalkyl wherein the alkyl moiety has 1 to 6 carbon atoms, preferably 1 to 4 carbon atoms, or aralkyl wherein the alkyl moiety has 1 to 6 carbon atoms, preferably 1 to 4 carbon atoms, and the aryl moiety has 6 to 10 carbon atoms.

Preferred starting cyano compounds are for example, acetonitrile, isobutyronitrile, acrylonitrile, crotononitrile, benzoic nitrile, benzylcyanide, adiponitrile, terephthalic acid dinitrile and cyanopyridine.

If a dicyano compound is used as the starting cyano compound, then, beside the 2-substituted pyridines carrying a cyano group on the substituent, the corresponding dipyridyl derivatives, such as, for example, from terephthaloyl dinitrile 2-(p-cyanophenyl)pyridine/p-dipyridyl (2)-benzol or from adiponitrile δ-pyridyl (2)-valeronitrile/α,ω-dipyridyl (2)-butane, are obtained.

In order to carry out the process of this invention, the corresponding cyano compound and 0.1 to 1 mole percent of cobaltocene are saturated in a pressure vessel with 3 to 20 atm. of acetylene, preferable 6 to 12 atm., and are heated to 80° to 200° C., preferably 100° to 180° C. Reacted acetylene is replaced by repressing by charges or continuously from a pressure flask. By suitable selection of the catalyst quantity, the pressure and the temperature within the stated limits, more than 20 moles of cyano compound can be reacted per mole of catalyst per hour. In the case of conversions up to 95 percent of the cyano compound, less than 10 mole percent of benzol is obtained, related to the pertinent 2-substituted pyridine.

Preferably, the reaction mixture is worked up by distillation. Unconverted cyano compound obtained from a first run, possible also a mixture containing benzol, can again be used in further preparations of the reaction mixture.

Normally no solvent is required for carrying out the reaction, however for better heat flow, inert solvents, for example, benzol or the pyridine compound to be produced, can be used as diluents in the case of the exothermal reaction.

The process can also be carried out continuously, for example, in a flow pipe.

A first particularly preferred embodiment of this invention involves a process for the catalytic production of β-substituted 2-ethyl pyridines from the (i) corresponding cyano ethyl compounds of amines and alcohols and (ii) acetylene. The conversion is carried out in the presence of cobaltocene. A particular advantage in using cobaltocene as a catalyst is that the catalyst cobaltocene can be used at a temperature above 80° C.

Such corresponding β-cyano ethyl compounds of amines or alcohols, as is well known, are easily obtained by the simple reaction of amines or alcohols with acrylonitrile. Such amines encompass ammonia, primary amines and secondary amines, preferably secondary aliphatic amines. Such alcohols encompass basically cyano-ethylizable organic hydroxy compounds which have no oxidizing effect on cobaltocene, and are preferably aliphatic alcohols having a small number of carbon atoms. Preferred β-cyanoethyl compounds are those of dimethylamine, diethylamine, piperdine and methanol.

In order to conduct the process of the first particularly preferred embodiment of this invention, the corresponding cyanoethyl compound and 0.1 to 1 mole percent of cobaltocene are saturated in a pressure vessel with 3 to 20 atm. of acetylene, preferably 6 to 12 atm., and are heated to 80° to 200° C., preferably 100° to 180° C. Coverted acetylene is replaced by pressing by charges or continuously from a pressure flask. By suitable selection of the catalyst quantity, pressure and temperature in the stated limits, more than 20 moles of cyano compound can be reacted per mole of catalyst per hour. In case of conversions up to 95 percent of the cyano compound, less than 10 mole percent related to the pertinent 2-substituted pyridine of benzol is obtained.

Preferably, the reaction mixtures are processed by distillation. A first run obtained thereby from unconverted cyano compound, possibly also a mixture with benzene, can again be used in the case of addition batches.

For carrying out the reaction, normally no solvent is needed.

But for better heat flow in the case of the exothermal reaction, inert solvents for example, benzene or the pyridine compound to be produced, can be used as diluents. The cyano ethyl compounds can be used either as a pure product or as a raw product mixed with the amine or alcohol.

The first particularily preferred embodiment of the process of this invention can also be carried out continuously, for example, in a flow pipe.

A second particularly preferred embodiment of this invention involves a process for the production of 2-N,N-disubstituted aminopyridines having the general formula:

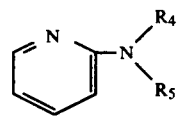

wherein $R_4$ and $R_5$ is alkyl having 1 to 6 carbon atoms, cycloalkyl having 3 to 9 carbon atoms, or aryl having 6 to 10 carbon atoms, or

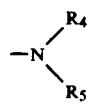

is piperidyl, pyrrolidyl or morpholyl.

In the process, a N,N-disubstituted cyanamide having the general formula:

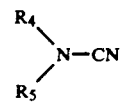

in which $R_4$, $R_5$ and

are the same as defined above, is reacted with acetylene in the presence of cobaltocene (as a catalyst) at elevated pressure and temperature.

The compound bis-cyclopentadienylcobalt, which is designated cobaltocene, is a catalyst which is easy to handle and can easily be produced from simple educts. A particular advantage resulting from the use of cobaltocene as a catalyst is that such catalyst can be used at high temperature above 80° C. Thus quicker and more complete conversions of the cyano compound are achieved without favoring the known side reactions of acetylene with itself to benzol and polymers.

Preferably the N,N-disubstituted cyanamide is N,N-dimethylcyanamide, N,N-dicyclohexylcyanamide, N-methyl,N-(β-cyanoethyl)-cyanamide, N-methyl,N-phenylcyanamide, N-methyl,N-cyclohexyl-cyanamide, N-cyanopiperidine, N-cyanopyrolidine or N-cyanomorpholine.

The N,N-dialkylcyanamides may be easily produced in a known manner from chlorine cyanides and the corresponding secondary amines as described, for example, in Belgium Patent No. 641,601.

In order to carry out the process of this invention, the corresponding cyanamide compound and cobaltocene is usually saturated in a pressure vessel with acetylene and the admixture is heated. Preferably the conversion is carried out at a pressure of 10 to 25 bar and at a temperature of 70° to 180° C. Preferably the quantity of cobaltocene used is 0.5 to 2.0 percent by weight related to the cyanamide used. Converted acetylene is replaced by more acetylene by charges thereof or continuous feeding thereof. As a result of the use of the quantity of catalyst and of pressure and temperature within the stated limits, more than 20 mole of cyano compound per mole of catalyst and per hour can be converted.

Effectively, the reaction batches are worked up (processed) by distillation. The first distillation runnings obtained thereby are unconverted cyano compound, possible also in mixture with benzol, which can be used again in other batches. For execution of the reaction, normally no solvent is required; however, for better heat discharge during the exothermal reaction, an inert solvent, for example, benzol, or a pyridine compound to be produced, can be used as a diluent.

The process can also be carried out continuously, for example, in a flow pipe.

DETAILED DESCRIPTION OF THIS INVENTION

As used herein, an alkyl group (or moiety) of 1 to 4 carbon atoms can be, for example, methyl, ethyl, butyl, propyl, isopropyl, isobutyl, sec-butyl or t-butyl.

As used herein, an alkyl group (or moiety) of 1 to 6 carbon atoms can be, for example, methyl, ethyl, butyl, propyl, isopropyl, isobutyl, sec-butyl, t-butyl, amyl, isoamyl, 2-pentyl, 3-pentyl, t-amyl, 3-methyl-2-butyl, 2-methyl-1-butyl, hexyl, 2-methyl-1-pentyl, 3-methyl-1-pentyl, isohexyl, 2-ethyl-1-butyl, 2-hexyl, 3-hexyl, 3-methyl-2-pentyl, 2,3-dimethyl-1-butyl, 4-methyl-2-pentyl, 2-methyl-3-pentyl, 2,2-dimethyl-3-butyl, 2-methyl-2-pentyl, 2,3-dimethyl-2-butyl or 3-methyl-3-pentyl.

As used herein, an alkyl group (or moiety) of 1 to 8 carbon atoms can be, for example, methyl, ethyl, butyl, propyl, isopropyl, isobutyl, sec-butyl, t-butyl, amyl, isoamyl, 2-pentyl, 3-pentyl, t-amyl, 3-methyl-2-butyl, 2-methyl-1-butyl, hexyl, 2-methyl-1-pentyl, 3-methyl-1-pentyl, isohexyl, 2-ethyl-1-butyl, 2-hexyl, 3-hexyl, 3-methyl-2-pentyl, 2,3-dimethyl-1-butyl, 4-methyl-2-pentyl, 2-methyl-3-pentyl, 2,2-dimethyl-3-butyl, 2-methyl-2-pentyl, 2,3-dimethyl-2-butyl, 3-methyl-3-pentyl, heptyl, 2,4-dimethyl-3-pentyl, 2,4-dimethyl-1-pentyl, 4-methyl-1-hexyl, 2,3,3-trimethyl-2-butyl, octyl or 2-octyl.

As used herein, an aryl group (or moiety) having 6 to 10 carbon atoms can be for example, phenyl, 1-naphthyl or 2-naphthyl.

As used herein, a cycloalkyl group (or moiety) having 3 to 9 carbon atoms can be, for example, cyclobutyl, cycloheptyl, cyclohexyl, 1,3-dimethyl cyclohexyl, 1,4-dimethyl cyclohexyl, isopropyl cyclohexyl, 1,3,5-trimethyl cyclohexyl, cyclopentyl or methyl cyclohexyl.

As used herein, an alkenyl group (or moiety) $C_nH_{2n-1}$, having 2 to 8 carbon atoms can be, for example, propenyl, ethenyl, pentenyl, 1-butenyl, 3-butenyl, 2-butenyl, hexenyl, octenyl or heptenyl.

As used herein, an aliphatic alcohol having a small number of carbon atoms which has no oxidizing effect, for example, has one to 8 carbon atoms. Such aliphatic alcohols can be, for example, methanol, ethanol, n-propyl alcohol, isopropyl alcohol, n-butyl alcohol, isobutyl alcohol, sec. butyl alcohol, tertiary butyl alcohol, n-amyl alcohol, isoamyl alcohol, 2-methyl-1-butanol, neopentyl alcohol, t-amyl alcohol, 2-pentanol, 3-pentanol, 3-methyl-2-butanol, n-hexyl alcohol, 2-methyl-1-pentanol, 3-methyl-1-pentanol, isohexyl alcohol, 2,4-dimethyl-1-pentanol, 1-octanol, 2-octanol, 2,3-dimethyl-3-pentanol, pentamethylethanol, 2-methyl-2-pentanol, n-heptyl alcohol, 2-ethyl-1-butanol, 2-hexanol, 3-hexanol, 3-methyl-2-pentanol, 5-methyl-2-pentanol, 3-methyl-2-pentanol, 2,3-dimethyl-1-butanol, 3,3-dimethyl-1-butanol or 2,2-dimethyl-3-butanol.

As used herein, a primary amine, wherein the alkyl group (or moiety) has 1 to 8 carbon atoms, can be, for example, methyl amine, ethyl amine, n-butyl amine, n-amyl amine, octyl amine or isopropyl amine.

As used herein, a secondary aliphatic amine, wherein each alkyl group (or moiety) has 1 to 8 carbon atoms, can be, for example, diethyl amine, dimethyl amine, butyl ethyl amine, sec-butyl ethyl amine, dibutyl amine, diheptyl amine, dihexyl amine, dipropyl amine, diisopropyl amine, di-2-octyl amine, diisobutyl amine, dioctyl amine, dipentyl amine or ethyl methyl amine.

As used herein, a secondary amine can be, for example, any of the above secondary aliphatic amines, piperidine, pyrrole, pyrroline, pyrrolidine, benzyl 2-tolyl amine, benzyl 3-tolyl amine, benzyl 4-tolyl amine, dibenzyl amine, diphenyl amine, dicyclohexyl amine di-2-tolyl amine or methyl phenyl amine.

As used herein, a pyridyl group can be, for example, 2-pyridyl, 3-pyridyl, 4-pyridyl, 2-(3-methyl pyridyl) or 2-(5-ethyl pyridyl).

As used herein, all parts, ratios, and percentages are on a weight basis unless otherwise stated herein or otherwise obvious herefrom to one ordinarily skilled in the art. This invention is described in more detail by the subsequent numbered examples. The yields relate to the cyano compound used. If not specifically mentioned, the conversions of the cyano compounds were better than 99 percent.

EXAMPLE 1

1.1 gm. of cobaltocene (0.006 mole) was dissolved under nitrogen in 38.8 gm. of acetonitrile (0.946 mole). The material was stirred in a 1-liter autoclave at 12 atm. pressure of acetylene and at 175° C. for 7.5 hours. After the mixture was allowed to cool and relax (depressurized), it was distilled in a simple Vigreux column. From 93. gm of raw product, and after first runnings from acetonitrile and benzol, 67.6 gm. of 2-picoline having a purity of 99.5 percent was obtained - this corresponded to a yield of 76.4 percent of pure product.

EXAMPLE 2

A solution of 0.2 gm. (0.001 mole) of cobaltocene in 39.5 gm. (0.963 mole) of acetonitrile was saturated at room temperature in a stirring autoclave with 11.5 atm. of acetylene and heated to 180° C. within 1 hour. After the pressure had dropped in 2 hours from 26 to 8 atm., the reaction was allowed to continue for 4 hours at 11.5 atm. of acetylene pressure. After the reaction mixture was allowed to cool and the pressure dropped to atmospheric, the raw product was distilled. 6 gm. of a mixture of 81.6 percent of benzol and 18.2 percent of acetonitrile and 73.9 gm. of 2-picoline was obtained. The 2-picoline had a purity of 99.6 percent. This corresponded to a conversion of 97.2 percent of acetonitrile, a yield of 82.2 percent of 2-picoline and the formation of 7.9 mole percent of benzol.

EXAMPLE 3

Analogously to Example 1, 17.7 gm. of acrylonitrile (0.333 mole) and 0.5 gm. (0.003 mole) of cobaltocene in 45.1 gm. of benzol (i.e., benzene) were reacted with 12 atm. of acetylene at 120° C. for 60 min. and subsequently vacuum distilled. 12.4 gm. of 2-vinylpyridine was obtained having a purity of 97.1 percent, which corresponded to a yield of 34.4 percent. In addition, 3.1 gm. of acrylonitrile was recaptured—this corresponded to a conversion of about 83 percent.

EXAMPLE 4

Analogously to Example 1, 43.7 gm. of benzylcyanide (0.373 mole) with 0.5 gm. of cobaltocene (0.003 mole) was saturated at 12 atm. with acetylene and was heated for 2 hrs. to and at 175° C. After cooling, the reaction mixture was relaxed from 5.5 atm. to standard pressure, and distilled. 43.3 gm. of 2-benzylpyridine having a purity of 98.8 percent was obtained - this corresponded to a yield of 68 percent.

EXAMPLE 5

3.6 atm. of acetylene was pressed onto a solution of 2.8 gm. (0.015 mole) of cobaltocene in 115.3 gm. (1.67 mole) of isobutyronitril in a 1-liter stirring autoclave. Subsequently, the reaction mixture was heated in 60 minutes to 170° C. and was stirred for 5 hours with continuous addition of acetylene from an 11.5 atm. pressure bottle. By flash distillation, 179.4 gm. of a mixture of 5.7 percent of benzol, 2.1 percent of i-butyronitrile and 91.9 percent of 2-isopropyl pyridine was obtained. This corresponded to 96.7 percent of converted isobutyronitrile, an 81 percent yield and a formation of 9.7 mole percent of benzol, related to isopropylpyridine.

EXAMPLE 6

A solution of 25.0 gm. of 3-cyanopyridine (0.24 mole) and 0.4 gm. of cobaltocene (0.002 mole) in 25 ml. of benzol was heated in a stirring autoclave. After 12 atm. of acetylene had been inserted (pressed on) for 3 hrs. to and at 180° C., 27 gm. of 99.2 percent 2,3'-dipyridile was obtained by distillation. This corresponsed to a yield of 71.4 percent.

EXAMPLE 7

Analogously to Example 1, 49.9 gm. of benzonitrile (0.484 mole) and 0.8 gm. of cobaltocene (0.004 mole) was heated with 12 atm. of acetylene to and at 160° C. 59 gm. of 99.6 percent 2-phenylpyridine was obtained—this corresponded to 78.3 percent of theory.

EXAMPLE 8

Analogously to Example 5, 0.7 gm. of cobaltocene in 36.6 gm. of crotonic acid nitrile at 165° C. for 6 hours was treated with acetylene. After this the reaction mixture was allowed to cool, relaxed to atmospheric pressure and flash distilled in a vacuum. 48.5 gm. of a colorless condensate was obtained which, according to gas chromatography, contained 5.4 percent of benzol, 6.4 percent of crotonic acid nitrile and 70.1 percent of 2-propenylpyridine as the cis-trans isomer mixture. The conversion was about 92 percent; the yield was about 52.3 percent.

EXAMPLE 9

0.4 gm. of cobaltocene was dissolved in 20.8 gm. of benzol and 16.0 gm. of methacrylonitrile. The mixture was placed in an autoclave, saturated with 12 atm. of acetylene at 25° C. and heated to and at 150° C. for 6 hours. As in Example 8, 39.7 gm. of a condensate was obtained, which beside benzol contained 18.6 percent of methacrylonitrile and 24.6 percent of 2-isopropenyl pyridine. The conversion was about 54 percent; the yield was about 34.4 percent.

EXAMPLE 10

0.6 gm. of cobaltocene in 43 gm. of benzol was treated in an autoclave (while excluding air) with 39.8 gm. of 4-cyanopyridine. The mixture was saturated with 12 atm. of acetylene and heated to 180° C. After 2 hours the autoclave was cooled. Again 12 atm. of acetylene was pressed on, and the mixture was heated another 4 hours to and at 180° C. After allowing the reaction mixture to cool and unstress (depressurize), 41.5 gm. of a fraction was obtained by distillation (Kp 120°–130° C./0.02 torr). The fraction contained 9.2 percent of 4-cyanopyridine and 90.7 percent of 2,4'-dipyridyl. 2,4'-dipyridyl was isolated by recrystallization of this fraction from ligroin. The conversion was 90.4 percent; the yield was 63.0 percent.

EXAMPLE 11

As in Example 10, 27.1 gm. of benzol, 0.5 gm. of cobaltocene (catalyst) and 30.0 gm. of terephthalic acid nitrile were reacted with acetylene. After distilling off the benzol by vacuum distillation, 39.5 gm. of a sublimate was obtained. The sublimate contained about 9 percent of terephthalic acid nitrile, 70 percent of 4-(2-pyridyl)-benzoic nitrile and 21 percent of 1,4-di-(2-pyridyl)-benzol. The components were isolated using fractional sublimation and recrystallization from acetone.

EXAMPLE 12

37.9 gm. of adipic acid dinitrile and 0.7 gm. of cobaltocene was saturated in the autoclave at 20° C. at a pressure of 12 atm. and was heated to 180° C. This was cooled down to 30° C. after 60 minutes and acetylene was repressed (pressurized). After another 3 hours at 180° C., the reaction mixture was cooled and expanded. The fractional distillation of the reaction product resulted in 4.3 gm. of adipic acid nitrile, 28.8 gm. of $\omega$-(2-pyridyl)-valeronitrile and 14.7 gm. of $\alpha$-$\omega$-di-(2-pyridyl)-butane.

EXAMPLE 13

2.0 gm. of cobaltocene (0.01 mole) was dissolved under nitrogen in 175 gm. of $\beta$-diethylaminopropionitrile (1.4 mole). The mixture was saturated with 12 atm. of acetylene at 20° C. in a 1-liter autoclave. The admixture was heated to 125° C. and an exothermal reaction was observed. After the pressure dropped to 11 atm., the admixture was stirred for 6 hours at a constant acetylene pressure of 12 atm and at a temperature of 175° C. After allowing the mixture to cool and relax (depressurize), which was distilled in a column. After first runnings from benzene and a small quantity of starting product, 211 gm. of 2-($\beta$-diethylamineethyl)-pyridine was obtained. The 2-($\beta$-diethylamineethyl)-pyridine had a purity of 99.3 percent that corresponded to a yield of 84.7 percent.

EXAMPLE 14

1.0 gm. of cobaltocene (0.005 mole) and 71.5 gm. of $\beta$-dimethylaminopropionitrile (0.7 mole) was saturated with 12 atm. of acetylene at 20° C. (as in Example 13) and heated to 170° C. The admixture was stirred for another hour at a constant acetylene pressure of 12 atm. after a pressure drop to 11 atm. Upon distillative processing of the reaction product, 4.4 gm. of benzol, 5 gm. of $\beta$-dimethylaminoproprionitrile and 80.1 gm. of 2-($\beta$-dimethylaminoethyl)-pyridine were obtained. This corresponded to a conversion of 93.0 percent of $\beta$-dimethylaminopropionitrile and a yield of 72.7 percent of 99.4 percent 2-($\beta$-dimethylaminoethyl)-pyridine.

EXAMPLE 15

As in Example 13, 119 gm. of $\beta$-(N)-piperidinopropionitrile (0.86 mole) and 12 atm. of acetylene were reacted using 1.3 gm. of cobaltocene (0.007 mole) at 180° C. for 5 hours. After subsequent distillation, 140.7 gm. of 99 percent of 2-[$\beta$-(N)-piperidinoethyl]-pyridine was obtained. This corresponded to a yield of 85.0 percent.

EXAMPLE 16

27.9 gm. of β-methoxypropionitrile (0.33 mole) and 0.6 gm. of cobaltocene (0.003 mole) was dissolved under a $N_2$-atmosphere in 166.5 gm. of dry benzol. The resultant darkened solution was saturated with 12 atm. of acetylene in an autoclave at 20° C. for 5 minutes and then heated for 10 hours to 155° C. During this time, the inside pressure in the autoclave decreased form 20 to 15 atm. After cooling, expanding and flash distillation under decreased pressure, a distillate was obtained which contained 31.1 percent of 2-(β-methoxyethyl)-pyridine, along with 0.2 percent of β-methoxypropionitrile. In the subsequent fractional distillation, 35.7 gm. of 2-(β-methoxyethyl)-pyridine was obtained which had a purity of 97.9 percent (this corresponded to a yield of 77.7 percent). 2-(β-methoxyethyl)-pyridine (which is known by the name methyridine or promintic) has excellent anthelmintic properties--its synthesis was greatly simplified by the process of this invention.

EXAMPLE 17

1.2 gm. of cobaltocene (0.006 mole) was dissolved in 73.5 gm. of β-aminopropionitrile. The admixture was saturated with 12 atm. of acetylene in an autoclave at 20° C. and heated to 155° C. for 4 hours. After cooling and expanding, the raw product was subjected to flash distillation at 0.1 torr. 60 gm. of distillate having a content of 1.6 percent of benzol, 72.2 percent of β-aminopropionitrile and 25.1 percent of 2-(β-aminoethyl)-pyridine was obtained. This corresponded to a conversion of 41.1 percent and a yield of 11.8 percent.

EXAMPLE 18

A mixture of 42.4 gm. of acrylonitrile (0.80 mole) and 100 gm. of diethylamine (1.4 mole) was heated for 16 hours to 50° C., mixed with 1.2 gm. of cobaltocene (0.006 mole) and treated with acetylene in an autoclave (as described in Example 13). During the subsequent distillation 119.2 gm. of 99.8 percent of 2-(β-diethylaminoethyl)-pyridine was obtained (besides excess diethylamine and small quantities of benzol). This corresponds to a yield of 83.6 percent.

EXAMPLE 19

3.1 gm. of cobaltocene (0.016 mole) under nitrogen was dissolved in 44.0 gm. of benzol. The solution mixed with 164 gm. of anhydrous N,N-dimethylcyanamide (2.3 moles). The reaction mixture was saturated with 12 atm. of acetylene at 20° C. in a 1-liter autoclave (with stirring). The reaction mixture was heated to 70° C. Then at the beginning of the exothermal reaction, the heating was carefully increased so that a temperature of 160° C. prevailed in the autoclave. After a drop in pressure in the autoclave to below 12 atm., acetylene was repressed on. After 10 hours of reaction time, the autoclave was cooled down and expansion allowed. As a result of fractional distillation, 238 gm. of 2-(N,N-dimethylamino)-pyridine (boiling point: 92° C., 21 torr) was obtained, after benzol and a small quantity of N,N-dimethylcyanamide had been obtained. The 2-(N,N-dimethylamino)-pyridine had a purity of 99.8 percent—this corresponded to a yield of 84.5 percent.

EXAMPLE 20

Analogously to Example 19, 1.0 gm. of cobaltocene (0.005 mole), 44.0 gm. of benzol and 99.1 gm. of anhydrous N-cyanopiperidine (0.9 mole) was treated in a 1-liter autoclave (with stirring) for 10 hours with acetylene at 70° C. to 170° C. The reaction product was distilled. Beside benzol, 10.3 gm. of N-cyanopiperidine and 116.2 gm. of 2-(N-piperidino)-pyridine were obtained. This corresponded to a yield of 79.6 percent.

EXAMPLE 21

Analogously to Example 19, 2.0 gm. of cobaltocene (0.011 mole), 180 gm. of 2-(N,N-dimethylamino)-pyridine and 57.5 gm. of anhydrous N,N-dimethylcyanamide (0.8 mole) was treated for 6 hours with acetylene at 125° to 170° C. 284 gm. of a raw product was obtained. After a small first run (separation) of benzol and N,N-dimethylcyanamide, 268.7 gm. of 2-(N,N-dimethylamino)-pyridine was obtained by fractional distillation. This corresponded to a yield of 88.5 percent or 84.8 percent, related to coverted acetylene.

EXAMPLE 22

Analogously to Example 19, 1.1 gm. of cobaltocene (0.006 mole) and 75.0 gm. of N-methyl-N-phenyl-cyanamide (0.57 mole) was treated with acetylene in a 1-liter autoclave (with stirring) hours at 120° to 170° C. From the reaction material, 55.2 gm. of educt and 15.5 gm. of 2-(N-methyl-N-phenylamino)-pyridine were obtained by distillation. This corresponded to a yield of 56 percent related to the converted cyano compound.

EXAMPLE 23

Using the process of Example 19, 46.4 gm. of 2-(N-pyrrolidino)-pyridine (61 percent yield) was obtained from 0.6 gm. of cobaltocene (0.003 mole), 70 ml of benzol and 49.2 gm. of N-cyanopyrrolidine (0.5 mole). The reaction was conducted with acetylene in a 1-liter autoclave (with stirring) for 8 hours at 130° to 170° C. Distillation was used to obtain the product from this reaction mixture.

Using the process of Example 19, 114.3 gm. of 2-(N-morpholino)-pyridine was obtained (78 percent yield) from 1.0 gm. of cobaltocene (0.005 mole), 150 ml of benzol and 100 gm. of N-cyanomorpholine (0.89 mole). The reaction was conducted for 7 hours at 80° to 160° C. Distillation was used to obtain the product from the reaction mixture.

What is claimed is:

1. A process for the catalytic production of a 2-N,N-disubstituted amino pyridine having the formula:

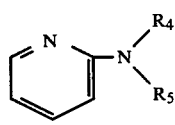

which comprises reacting a cyano compound and acetylene in the presence of cobaltocene, which is a catalyt, said reaction being conducted at a pressure between 3 and 20 atmospheres of acetylene, said cobaltocene not being converted to a different valance state during the process, and said cyano compound being a N,N-disubstituted cyanamide having the formula:

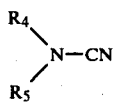

wherein $R_4$ and $R_5$ are alkyl having 1 to 6 carbon atoms, cycloalkyl having 3 to 9 carbon atoms or aryl having 6 to 10 carbon atoms, or

is piperidino, pyrrolidino or morpholino, whereby said 2-N,N-disubstituted amino piperidine results.

2. Process as claimed in claim 1 wherein said reaction is conducted at elevated pressure and temperature.

3. Process as claimed in claim 1 wherein said reaction is conducted continuously in a flow pipe.

4. Process as claimed in claim 1 wherein N,N-disubstituted cyanamide is N,N-dimethylcyanamide, N,N-dicyclohexylcyanamide, N-methyl,N-($\beta$-cyanoethyl)-cyanamide, N-methyl,N-phenylcyanamide, N-methyl,N-cyclohexylcyanamide, N-cyanopiperidine, N-cyanopyrrolidine or N-cyanomorpholine.

5. Process as claimed in claim 1 wherein said reaction is carried out at a pressure of 10 to 25 bar and at a temperature of 70° to 180° C.

6. Process as claimed in claim 1 wherein 0.5 to 2.0 percent by weight of said cobaltocene, related to said cyanamide, is used.

7. Process as claimed in claim 1 wherein an inert solvent is present.

8. Process as claimed in claim 1 wherein some of the pyridine product is present as a diluent for the reaction.

9. Process as claimed in claim 1 wherein said aminopyridine and cobaltocene are saturated with acetylene and the admixture is heated to the reaction temperature.

10. Process as claimed in claim 9 wherein said acetylene is replaced with more acetylene as said acetylene is converted by charges or continuous feeding of acetylene.

11. Process as claimed in claim 1 wherein no inert solvent is present.

12. A process for the catalytic production of a 2-substitute pyridine which comprises reacting a cyano compound and acetylene in the presence of cobaltocene, which is a catalyst, said reaction being conducted at a pressure between 3 to 20 atmospheres of acetylene, said cobaltocene not being converted to a different valence state during the process, and said cyano compound being one whereby said 2-substituted pyridine results.

13. A process for the catalytic production of a 2-substituted pyridine which comprises reacting a cyano compound and acetylene in the presence of cobaltocene, which is a catalyst, said reaction being conducted at a pressure between 3 and 20 atmospheres of acetylene, said cobaltocene not being converted to a different valence state during the process, and said cyano compound being a $\beta$-cyano ethyl compound of an amine, whereby said 2-substituted pyridine results.

14. Process as claimed in claim 13 wherein said cyano compound is a $\beta$-cyano ethyl compound of ammonia.

15. Process as claimed in claim 13 wherein said cyano compound is a $\beta$-cyano ethyl compound of a primary amine or a secondary amine.

16. Process as claimed in claim 13 wherein said cyano compound is a $\beta$-cyano ethyl compound of a secondary aliphatic amine.

17. Process as claimed in claim 13 wherein said $\beta$-cyano ethyl compound of an amine is used as the raw product in a mixture with the corresponding amine.

18. A process for the catalytic production of a 2-substituted pyridine which comprises reacting a cyano compound and acetylene in the presence of cobaltocene, which is a catalyst, said reaction being conducted at a pressure between 3 and 20 atmospheres of acetylene, said cobaltocene not being converted to a different valance state during the process, and said cyano compound being a $\beta$-cyano ethyl compound of an alcohol, whereby said 2-substituted pyridine results.

19. Process as claimed in claim 18 wherein said cyano compound is a $\beta$-cyano ethyl compound of an aliphatic alcohol.

20. Process as claimed in claim 18 wherein said $\beta$-cyano ethyl compound of an amine or alcohol is a $\beta$-cyano ethyl compound of dimethyl amine, diethylamine, piperidine or methanol.

21. Process as claimed in claim 18 wherein said $\beta$-cyano ethyl compound of an alcohol is used as the raw product in a mixture with the corresponding alcohol.

* * * * *